(12) United States Patent
Jacobs et al.

(10) Patent No.: US 9,560,954 B2
(45) Date of Patent: Feb. 7, 2017

(54) CONNECTOR FOR USE WITH ENDOSCOPE

(75) Inventors: Charles Jacobs, Loganville, GA (US); Louis F. Malice, Jr., Marietta, GA (US); William Parks, Lawrenceville, GA (US)

(73) Assignee: EndoChoice, Inc., Alpharetta, GA (US)

( * ) Notice: Subject to any disclaimer, the term of this patent is extended or adjusted under 35 U.S.C. 154(b) by 152 days.

(21) Appl. No.: 13/557,114

(22) Filed: Jul. 24, 2012

(65) Prior Publication Data

US 2014/0031627 A1 Jan. 30, 2014

(51) Int. Cl.
*A61B 1/00* (2006.01)
*A61B 1/04* (2006.01)
*A61B 1/12* (2006.01)

(52) U.S. Cl.
CPC ........ *A61B 1/00112* (2013.01); *A61B 1/00119* (2013.01); *A61B 1/00121* (2013.01); *A61B 1/00128* (2013.01)

(58) Field of Classification Search
CPC ............. A61B 1/00119; A61B 1/00121; A61B 1/00128; A61B 1/00135; A61B 1/00137; A61B 1/00142; A61B 1/015; A61B 1/12; A61B 1/121; A61B 1/122; A61B 1/123; A61B 1/125; A61B 1/126; A61M 39/00
USPC ............... 600/121, 122, 123, 124, 125, 153, 154,600/132, 156–159
See application file for complete search history.

(56) References Cited

U.S. PATENT DOCUMENTS

| | | | |
|---|---|---|---|
| 4,084,401 A | 4/1978 | Belardi | |
| 4,253,448 A | 3/1981 | Terada | |
| 4,261,345 A | 4/1981 | Yamaguchi | |
| 4,402,313 A | 9/1983 | Yabe | |
| 4,414,608 A | 11/1983 | Furihata | |
| 4,439,030 A | 3/1984 | Ueda | |
| 4,469,090 A | 9/1984 | Konomura | |
| 4,494,549 A | 1/1985 | Namba | |
| 4,522,196 A | 6/1985 | Cunningham | |
| 4,565,423 A | 1/1986 | Ueda | |
| 4,576,144 A | 3/1986 | Ishii | |
| 4,588,294 A | 5/1986 | Siegmund | |
| 4,590,923 A | 5/1986 | Watanabe | |
| 4,641,635 A | 2/1987 | Yabe | |
| 4,699,463 A | 10/1987 | D'Amelio | |
| 4,708,126 A | 11/1987 | Toda | |

(Continued)

FOREIGN PATENT DOCUMENTS

CN 1376443 10/2002
CN 2829646 Y 10/2006

(Continued)

OTHER PUBLICATIONS

First Image of an Endo Smart Cap, made by Medivators, and obtained from http://www.byrnemedical.com/prod/145L.jpg and advertised at http://www.medivators.com/products/endoscopy-procedure-products/irrigation-tubing/endo-smartcap%C2%AE.

(Continued)

*Primary Examiner* — Ryan Henderson
(74) *Attorney, Agent, or Firm* — Novel IP; Hazim Ansari; Sona Dalal

(57) ABSTRACT

The present specification discloses a disposable tubing joint connector system which connects a tubing set and an endoscope. The connector embodiments disclosed herein include dual o-ring seals, in two separate channels, that enable an efficient and leak proof connection between two ports of an endoscope and corresponding flexible tubing.

15 Claims, 4 Drawing Sheets

(56) References Cited

U.S. PATENT DOCUMENTS

| | | |
|---|---|---|
| 4,727,859 A | 3/1988 | Lia |
| 4,736,732 A | 4/1988 | Shimonaka |
| 4,753,222 A | 6/1988 | Morishita |
| 4,764,001 A | 8/1988 | Yokota |
| 4,794,913 A | 1/1989 | Shimonaka |
| 4,801,792 A | 1/1989 | Yamasita |
| 4,841,952 A | 6/1989 | Sato |
| 4,846,154 A | 7/1989 | MacAnally |
| 4,868,644 A | 9/1989 | Yabe |
| 4,877,314 A | 10/1989 | Kanamori |
| 4,878,485 A | 11/1989 | Adair |
| 4,888,639 A | 12/1989 | Yabe |
| 4,902,115 A | 2/1990 | Takahashi |
| 4,905,670 A | 3/1990 | Adair |
| 4,914,521 A | 4/1990 | Adair |
| 4,974,075 A | 11/1990 | Nakajima |
| 4,976,522 A | 12/1990 | Igarashi |
| 4,982,724 A | 1/1991 | Saito |
| 4,984,878 A | 1/1991 | Miyano |
| 4,998,182 A | 3/1991 | Krauter |
| 5,166,787 A | 11/1992 | Irion |
| 5,193,525 A | 3/1993 | Silverstein |
| 5,239,983 A | 8/1993 | Katsurada |
| 5,296,971 A | 3/1994 | Mori |
| 5,299,561 A | 4/1994 | Yoshimoto |
| 5,305,121 A | 4/1994 | Moll |
| 5,309,227 A | 5/1994 | Inoue |
| 5,313,934 A | 5/1994 | Wiita |
| 5,339,800 A | 8/1994 | Wiita |
| 5,359,456 A | 10/1994 | Kikuchi |
| 5,380,049 A * | 1/1995 | Smowton ............... 285/148.2 |
| 5,398,056 A | 3/1995 | Yabe |
| 5,408,263 A | 4/1995 | Dolidon |
| 5,412,478 A | 5/1995 | Ishihara |
| 5,420,644 A | 5/1995 | Watanabe |
| 5,432,543 A | 7/1995 | Hasegawa |
| 5,436,767 A | 7/1995 | Suzuki |
| 5,447,148 A | 9/1995 | Oneda |
| 5,452,391 A | 9/1995 | Chou |
| 5,460,167 A | 10/1995 | Yabe |
| 5,483,951 A | 1/1996 | Frassica |
| 5,485,316 A | 1/1996 | Mori |
| 5,489,256 A | 2/1996 | Adair |
| 5,507,717 A | 4/1996 | Kura |
| 5,512,940 A | 4/1996 | Takasugi |
| 5,515,449 A | 5/1996 | Tsuruoka |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,550,582 A | 8/1996 | Takasugi |
| 5,585,840 A | 12/1996 | Watanabe |
| 5,587,839 A | 12/1996 | Miyano |
| 5,589,874 A | 12/1996 | Buchin |
| 5,592,216 A | 1/1997 | Uehara |
| 5,605,530 A | 2/1997 | Fischell |
| 5,609,560 A | 3/1997 | Ichikawa |
| 5,617,136 A | 4/1997 | Iso |
| 5,630,782 A | 5/1997 | Adair |
| 5,653,677 A | 8/1997 | Okada |
| 5,656,011 A | 8/1997 | Uihlein |
| 5,662,588 A | 9/1997 | Iida |
| 5,675,378 A | 10/1997 | Takasugi |
| 5,679,110 A | 10/1997 | Hamazaki |
| 5,685,823 A | 11/1997 | Ito |
| 5,701,155 A | 12/1997 | Wood |
| 5,702,345 A | 12/1997 | Wood |
| 5,702,347 A | 12/1997 | Yabe |
| 5,707,344 A | 1/1998 | Nakazawa |
| 5,716,323 A | 2/1998 | Lee |
| 5,725,474 A | 3/1998 | Yasui |
| 5,725,476 A | 3/1998 | Yasui |
| 5,725,477 A | 3/1998 | Yasui |
| 5,728,045 A | 3/1998 | Komi |
| 5,751,340 A | 5/1998 | Strobl |
| 5,764,809 A | 6/1998 | Nomami |
| 5,777,797 A | 7/1998 | Miyano |
| 5,782,751 A | 7/1998 | Matsuno |
| 5,793,539 A | 8/1998 | Konno |
| 5,800,341 A | 9/1998 | McKenna |
| 5,812,187 A | 9/1998 | Watanabe |
| 5,830,124 A | 11/1998 | Suzuki |
| 5,836,894 A | 11/1998 | Sarvazyan |
| 5,852,511 A | 12/1998 | Tateyama |
| 5,860,913 A | 1/1999 | Yamaya |
| 5,870,234 A | 2/1999 | EbbesmeierneeSchitthof |
| 5,871,439 A | 2/1999 | Takahashi |
| 5,871,440 A | 2/1999 | Okada |
| 5,876,326 A | 3/1999 | Takamura |
| 5,879,284 A | 3/1999 | Tsujita |
| 5,894,322 A | 4/1999 | Hamano |
| 5,912,764 A | 6/1999 | Togino |
| 5,913,817 A | 6/1999 | Lee |
| 5,914,810 A | 6/1999 | Watts |
| 5,916,148 A | 6/1999 | Tsuyuki |
| 5,929,901 A | 7/1999 | Adair |
| 5,930,424 A | 7/1999 | Heimberger |
| 5,933,275 A | 8/1999 | Igarashi |
| 5,933,282 A | 8/1999 | Tomioka |
| 5,936,773 A | 8/1999 | Togino |
| 5,940,126 A | 8/1999 | Kimura |
| 5,961,445 A | 10/1999 | Chikama |
| 5,969,888 A | 10/1999 | Sukekawa |
| 5,986,693 A | 11/1999 | Adair |
| 5,989,185 A | 11/1999 | Miyazaki |
| 5,993,037 A | 11/1999 | Tomioka |
| 5,995,136 A | 11/1999 | Hattori |
| 6,009,189 A | 12/1999 | Schaack |
| 6,025,873 A | 2/2000 | Nishioka |
| 6,043,839 A | 3/2000 | Adair |
| 6,069,698 A | 5/2000 | Ozawa |
| 6,080,104 A | 6/2000 | Ozawa |
| 6,104,540 A | 8/2000 | Hayakawa |
| 6,110,127 A | 8/2000 | Suzuki |
| 6,117,068 A | 9/2000 | Gourley |
| 6,124,989 A | 9/2000 | Oode |
| 6,139,175 A | 10/2000 | Tomioka |
| 6,139,490 A | 10/2000 | Breidenthal |
| 6,147,808 A | 11/2000 | Togino |
| 6,163,401 A | 12/2000 | Igarashi |
| 6,166,858 A | 12/2000 | Togino |
| 6,181,481 B1 | 1/2001 | Yamamoto |
| 6,184,923 B1 | 2/2001 | Miyazaki |
| 6,185,046 B1 | 2/2001 | Togino |
| 6,196,967 B1 | 3/2001 | Lim |
| 6,201,646 B1 | 3/2001 | Togino |
| 6,201,648 B1 | 3/2001 | Togino |
| 6,210,322 B1 * | 4/2001 | Byrne ............... 600/158 |
| 6,211,904 B1 | 4/2001 | Adair |
| 6,215,517 B1 | 4/2001 | Takahashi |
| 6,217,500 B1 | 4/2001 | Helseth |
| 6,245,086 B1 | 6/2001 | Storz |
| 6,249,391 B1 | 6/2001 | Hayakawa |
| 6,260,994 B1 | 7/2001 | Matsumoto |
| 6,261,226 B1 | 7/2001 | McKenna |
| 6,275,255 B1 | 8/2001 | Adair |
| 6,295,368 B1 | 9/2001 | Hasegawa |
| 6,306,082 B1 | 10/2001 | Takahashi |
| 6,310,642 B1 | 10/2001 | Adair |
| 6,310,736 B1 | 10/2001 | Togino |
| 6,315,712 B1 | 11/2001 | Rovegno |
| 6,322,496 B1 | 11/2001 | Iida |
| 6,327,094 B1 | 12/2001 | Aoki |
| 6,327,101 B1 | 12/2001 | Miyano |
| 6,334,845 B1 | 1/2002 | Higuchi |
| 6,353,504 B1 | 3/2002 | Yamamoto |
| 6,375,610 B2 | 4/2002 | Verschuur |
| 6,387,045 B1 | 5/2002 | Takahashi |
| 6,398,723 B1 | 6/2002 | Kehr |
| 6,400,514 B2 | 6/2002 | Minami |
| 6,422,995 B2 | 7/2002 | Akiba |
| 6,425,857 B1 | 7/2002 | Rudischhauser |
| 6,450,950 B2 | 9/2002 | Irion |
| 6,461,304 B1 | 10/2002 | Tanaka |

(56) References Cited

U.S. PATENT DOCUMENTS

| | | |
|---|---|---|
| 6,464,631 B1 | 10/2002 | Girke |
| 6,464,633 B1 | 10/2002 | Hosoda |
| 6,468,201 B1 | 10/2002 | Burdick |
| 6,468,202 B1 | 10/2002 | Irion |
| 6,471,636 B1 | 10/2002 | Sano |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,983 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 | 12/2004 | Stelzer |
| 6,844,985 B2 | 1/2005 | Murayama |
| 6,846,311 B2 | 1/2005 | Gatto |
| 6,849,043 B2 | 2/2005 | Kondo |
| 6,860,516 B2 * | 3/2005 | Ouchi et al. ............... 285/124.1 |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,829 B1 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,918,693 B2 | 7/2005 | Ota |
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |

(56) References Cited

U.S. PATENT DOCUMENTS

| | | |
|---|---|---|
| 7,542,069 B2 | 6/2009 | Tashiro |
| 7,553,276 B2 | 6/2009 | Iddan |
| 7,559,889 B2 | 7/2009 | Takahashi |
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 | 12/2009 | Yang |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 | 4/2010 | Lin |
| 7,725,013 B2 | 5/2010 | Sugimoto |
| 7,728,867 B2 | 6/2010 | Fukuyama |
| 7,734,160 B2 | 6/2010 | Sudo |
| 7,746,566 B2 | 6/2010 | Mizusawa |
| 7,746,572 B2 | 6/2010 | Asami |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irion |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donomae |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchimura |
| 7,918,788 B2 | 4/2011 | Lin |
| 7,938,773 B2 | 5/2011 | Kawai |
| 7,940,296 B2 | 5/2011 | Ogino |
| 7,942,814 B2 | 5/2011 | Remijan |
| 7,951,068 B2 | 5/2011 | Kura |
| 7,967,745 B2 | 6/2011 | Gilad |
| 7,976,462 B2 | 7/2011 | Wright |
| 7,995,093 B2 | 8/2011 | Takeuchi |
| 7,998,064 B2 | 8/2011 | Otawara |
| 8,002,696 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Noguchi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |
| 8,200,042 B2 | 6/2012 | Doi |
| 8,208,015 B2 | 6/2012 | Unsai |
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,558 B2 | 9/2012 | Sato |
| 8,262,565 B2 | 9/2012 | Okada |
| 8,279,275 B2 | 10/2012 | Gono |
| 8,295,566 B2 | 10/2012 | Nishimura |
| 8,300,325 B2 | 10/2012 | Katahira |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |
| 8,449,457 B2 | 5/2013 | Aizenfeld |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 8,764,642 B2 | 7/2014 | Bendele |
| 9,144,373 B2 | 9/2015 | Kaye |
| 2002/0007110 A1 | 1/2002 | Irion |
| 2002/0087047 A1 | 7/2002 | Remijan |
| 2002/0098732 A1 | 7/2002 | Shimizu |
| 2002/0109774 A1 | 8/2002 | Meron |
| 2002/0151768 A1 | 10/2002 | Akiba |

(56) References Cited

U.S. PATENT DOCUMENTS

| | | |
|---|---|---|
| 2002/0161281 A1 | 10/2002 | Jaffe |
| 2002/0161282 A1 | 10/2002 | Fulghum |
| 2002/0183591 A1 | 12/2002 | Matsuura |
| 2003/0030918 A1 | 2/2003 | Murayama |
| 2003/0032860 A1 | 2/2003 | Avni |
| 2003/0036681 A1 | 2/2003 | Aviv |
| 2003/0055314 A1 | 3/2003 | Petitto |
| 2003/0083552 A1 | 5/2003 | Remijan |
| 2003/0125788 A1 | 7/2003 | Long |
| 2003/0130564 A1 | 7/2003 | Martone |
| 2003/0139648 A1 | 7/2003 | Foley |
| 2003/0158462 A1 | 8/2003 | Takase |
| 2003/0181787 A1 | 9/2003 | Kondo |
| 2003/0199860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihalcik |
| 2004/0073120 A1 | 4/2004 | Motz |
| 2004/0104999 A1 | 6/2004 | Okada |
| 2004/0111012 A1 | 6/2004 | Whitman |
| 2004/0133076 A1 | 7/2004 | Kobayashi |
| 2004/0138532 A1 | 7/2004 | Glukhovsky |
| 2004/0143162 A1 | 7/2004 | Krattiger |
| 2004/0158129 A1 | 8/2004 | Okada |
| 2004/0160682 A1 | 8/2004 | Miyano |
| 2004/0176661 A1 | 9/2004 | Futatsugi |
| 2004/0190159 A1 | 9/2004 | Hasegawa |
| 2004/0210113 A1 | 10/2004 | Hasegawa |
| 2004/0220451 A1 | 11/2004 | Gravenstein |
| 2004/0242958 A1 | 12/2004 | Fujikawa |
| 2004/0242961 A1 | 12/2004 | Bughici |
| 2004/0249247 A1 | 12/2004 | Iddan |
| 2004/0254423 A1 | 12/2004 | Wendlandt |
| 2004/0267093 A1 | 12/2004 | Miyagi |
| 2005/0020876 A1 | 1/2005 | Shioda |
| 2005/0027164 A1 | 2/2005 | Barbato |
| 2005/0038317 A1 | 2/2005 | Ratnakar |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1 | 4/2005 | Okada |
| 2005/0096501 A1 | 5/2005 | Stelzer |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |
| 2005/0234296 A1 | 10/2005 | Saadat |
| 2005/0234347 A1 | 10/2005 | Yamataka |
| 2005/0251127 A1 | 11/2005 | Brosch |
| 2005/0256376 A1* | 11/2005 | Bar-Or et al. ............... 600/156 |
| 2005/0261553 A1 | 11/2005 | Swain |
| 2005/0272975 A1 | 12/2005 | McWeeney |
| 2005/0283048 A1 | 12/2005 | Gill |
| 2005/0284491 A1 | 12/2005 | Tashiro |
| 2006/0047184 A1 | 3/2006 | Banik |
| 2006/0052663 A1 | 3/2006 | Koitabashi |
| 2006/0063976 A1 | 3/2006 | Aizenfeld |
| 2006/0069307 A1 | 3/2006 | Boulais |
| 2006/0069314 A1 | 3/2006 | Farr |
| 2006/0149129 A1 | 7/2006 | Watts |
| 2006/0173244 A1 | 8/2006 | Boulais |
| 2006/0183971 A1 | 8/2006 | Haviv |
| 2006/0183975 A1 | 8/2006 | Saadat |
| 2006/0189845 A1 | 8/2006 | Maahs |
| 2006/0211916 A1 | 9/2006 | Kasahara |
| 2006/0217594 A1 | 9/2006 | Ferguson |
| 2006/0224040 A1 | 10/2006 | Khait |
| 2006/0229499 A1 | 10/2006 | Eisenkolb |
| 2006/0241347 A1 | 10/2006 | Whitehead |
| 2006/0252994 A1 | 11/2006 | Ratnakar |
| 2006/0264704 A1 | 11/2006 | Fujimori |
| 2006/0293556 A1 | 12/2006 | Garner |
| 2006/0293562 A1 | 12/2006 | Uchimura |
| 2007/0015964 A1 | 1/2007 | Eversull |
| 2007/0015968 A1 | 1/2007 | Shelnutt |
| 2007/0019916 A1 | 1/2007 | Takami |
| 2007/0020694 A1 | 1/2007 | Pickford |
| 2007/0030345 A1 | 2/2007 | Amling |
| 2007/0049803 A1 | 3/2007 | Moriyama |
| 2007/0055100 A1 | 3/2007 | Kato |
| 2007/0073109 A1 | 3/2007 | Irion |
| 2007/0078304 A1 | 4/2007 | Shimizu |
| 2007/0083081 A1 | 4/2007 | Schlagenhauf |
| 2007/0100206 A1 | 5/2007 | Lin |
| 2007/0106119 A1 | 5/2007 | Hirata |
| 2007/0115376 A1 | 5/2007 | Igarashi |
| 2007/0118019 A1 | 5/2007 | Mitani |
| 2007/0123748 A1 | 5/2007 | Meglan |
| 2007/0142711 A1 | 6/2007 | Bayer |
| 2007/0162095 A1 | 7/2007 | Kimmel |
| 2007/0167673 A1 | 7/2007 | Enomoto |
| 2007/0167681 A1 | 7/2007 | Gill |
| 2007/0173686 A1 | 7/2007 | Lin |
| 2007/0173687 A1 | 7/2007 | Shima |
| 2007/0177008 A1 | 8/2007 | Bayer |
| 2007/0177009 A1 | 8/2007 | Bayer |
| 2007/0185384 A1 | 8/2007 | Bayer |
| 2007/0197875 A1 | 8/2007 | Osaka |
| 2007/0203396 A1 | 8/2007 | McCutcheon |
| 2007/0206945 A1 | 9/2007 | DeLorme |
| 2007/0208225 A1 | 9/2007 | Czaniera |
| 2007/0213590 A1 | 9/2007 | Squicciarini |
| 2007/0213591 A1 | 9/2007 | Aizenfeld |
| 2007/0225556 A1 | 9/2007 | Ortiz |
| 2007/0225565 A1 | 9/2007 | Ogino |
| 2007/0229656 A1 | 10/2007 | Khait |
| 2007/0244353 A1 | 10/2007 | Larsen |
| 2007/0244362 A1 | 10/2007 | El-Hachem |
| 2007/0244366 A1 | 10/2007 | Murata |
| 2007/0249899 A1 | 10/2007 | Seifert |
| 2007/0265498 A1 | 11/2007 | Ito |
| 2007/0282165 A1 | 12/2007 | Hopkins |
| 2007/0293720 A1 | 12/2007 | Bayer |
| 2008/0009672 A1 | 1/2008 | Krattiger |
| 2008/0021274 A1 | 1/2008 | Bayer |
| 2008/0021281 A1 | 1/2008 | Fujimori |
| 2008/0039689 A1 | 2/2008 | Yoshimitsu |
| 2008/0039693 A1 | 2/2008 | Karasawa |
| 2008/0045797 A1 | 2/2008 | Yasushi |
| 2008/0051628 A1 | 2/2008 | Pecherer |
| 2008/0051629 A1 | 2/2008 | Sugiyama |
| 2008/0051655 A1 | 2/2008 | Sato |
| 2008/0058595 A1 | 3/2008 | Snoke |
| 2008/0058598 A1 | 3/2008 | Ries |
| 2008/0058601 A1 | 3/2008 | Fujimori |
| 2008/0064931 A1 | 3/2008 | Schena |
| 2008/0065127 A1 | 3/2008 | Adams |
| 2008/0071290 A1 | 3/2008 | Larkin |
| 2008/0100699 A1 | 5/2008 | Hibi |
| 2008/0130108 A1 | 6/2008 | Bayer |
| 2008/0139881 A1 | 6/2008 | Cover |
| 2008/0163652 A1 | 7/2008 | Shatskin |
| 2008/0167529 A1 | 7/2008 | Otawara |
| 2008/0171910 A1 | 7/2008 | Kanazawa |
| 2008/0177139 A1 | 7/2008 | Courtney |
| 2008/0177140 A1 | 7/2008 | Cline |
| 2008/0188715 A1 | 8/2008 | Fujimoto |
| 2008/0221388 A1 | 9/2008 | Seibel et al. |
| 2008/0225134 A1 | 9/2008 | Amling |
| 2008/0255425 A1 | 10/2008 | Voegele |
| 2008/0262302 A1 | 10/2008 | Azarbarzin |
| 2008/0262312 A1 | 10/2008 | Carroll |
| 2008/0312497 A1 | 12/2008 | Elmouelhi |
| 2009/0005643 A1 | 1/2009 | Smith |
| 2009/0054790 A1 | 2/2009 | Czaniera |
| 2009/0062615 A1 | 3/2009 | Yamaya |
| 2009/0086017 A1 | 4/2009 | Miyano |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0161234 A1 | 6/2009 | Sasamoto |
| 2009/0163769 A1 | 6/2009 | Robertson |

(56) References Cited

U.S. PATENT DOCUMENTS

| | | |
|---|---|---|
| 2009/0209811 A1 | 8/2009 | Higuchi |
| 2009/0216084 A1 | 8/2009 | Yamane |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |
| 2009/0287192 A1 | 11/2009 | Vivenzio |
| 2009/0290236 A1 | 11/2009 | Wang |
| 2009/0299144 A1 | 12/2009 | Shigemori |
| 2009/0306474 A1 | 12/2009 | Wilson |
| 2009/0306476 A1 | 12/2009 | Banik |
| 2009/0318757 A1 | 12/2009 | Singh |
| 2010/0010301 A1 | 1/2010 | Hale |
| 2010/0010302 A1 | 1/2010 | Hadani |
| 2010/0013914 A1 | 1/2010 | Bettesh |
| 2010/0016673 A1 | 1/2010 | Bandy |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1 | 3/2010 | Takasugi |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1 | 5/2010 | Fujiwara |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0245653 A1 | 9/2010 | Bodor |
| 2010/0249496 A1 | 9/2010 | Cardenas |
| 2010/0249513 A1 | 9/2010 | Tydlaska |
| 2010/0256447 A1 | 10/2010 | Dubi |
| 2010/0286475 A1 | 11/2010 | Robertson |
| 2010/0296178 A1 | 11/2010 | Genet |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2011/0028790 A1 | 2/2011 | Farr |
| 2011/0054256 A1* | 3/2011 | Cushner et al. ............... 600/156 |
| 2011/0112363 A1 | 5/2011 | Koga |
| 2011/0160530 A1 | 6/2011 | Ratnakar |
| 2011/0169931 A1 | 7/2011 | Pascal |
| 2011/0184243 A1 | 7/2011 | Wright |
| 2011/0196200 A1 | 8/2011 | Glozman |
| 2011/0196204 A1 | 8/2011 | Setty |
| 2011/0211267 A1 | 9/2011 | Takato |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gettman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1 | 3/2012 | Takato |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1* | 4/2012 | Bendele et al. ............... 604/26 |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1 | 5/2013 | Menabde |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0253272 A1 | 9/2013 | Takahashi |
| 2013/0267778 A1 | 10/2013 | Rehe |
| 2013/0296649 A1 | 11/2013 | Kirma |
| 2013/0314521 A1 | 11/2013 | Satake |
| 2013/0317295 A1 | 11/2013 | Morse |
| 2014/0364691 A1 | 12/2014 | Krivopisk |

FOREIGN PATENT DOCUMENTS

| | | |
|---|---|---|
| CN | 1988841 | 6/2007 |
| CN | 2936129 Y | 8/2007 |
| CN | 101061940 A | 10/2007 |
| CN | 201108422 Y | 9/2008 |
| CN | 101385633 A | 3/2009 |
| CN | 101396258 | 4/2009 |
| CN | 101926171 | 12/2010 |
| CN | 102058375 A | 5/2011 |
| CN | 102058380 A | 5/2011 |
| CN | 101061940 | 6/2011 |
| CN | 201870615 U | 6/2011 |
| CN | 102469924 | 5/2012 |
| DE | 102005008153 A1 | 11/2005 |
| EP | 0029555 A2 | 6/1981 |
| EP | 543738 A1 | 5/1993 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1535565 | 6/2005 |
| EP | 1073365 B1 | 7/2005 |
| EP | 1627595 A1 | 2/2006 |
| EP | 668738 B1 | 6/2006 |
| EP | 1685790 A1 | 8/2006 |

(56) References Cited

FOREIGN PATENT DOCUMENTS

| | | |
|---|---|---|
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |
| EP | 2501271 A1 | 9/2012 |
| EP | 2503933 A1 | 10/2012 |
| EP | 2512577 A2 | 10/2012 |
| EP | 2529660 A1 | 12/2012 |
| EP | 2596756 A1 | 5/2013 |
| EP | 2623019 A1 | 8/2013 |
| GB | 2321132 | 7/1998 |
| GB | 2352922 A | 2/2001 |
| JP | 55078932 | 6/1980 |
| JP | 61055657 | 11/1986 |
| JP | 6359332 | 11/1988 |
| JP | H02188709 A | 7/1990 |
| JP | 5049000594 | 3/1993 |
| JP | H05309069 | 11/1993 |
| JP | 6105000800 | 4/1994 |
| JP | 7000000352 | 1/1995 |
| JP | 8122000657 | 5/1996 |
| JP | 1013007179 | 4/1998 |
| JP | 1015001113 | 6/1998 |
| JP | 11125773 | 5/1999 |
| JP | 11137512 | 5/1999 |
| JP | H11125773 A | 5/1999 |
| JP | 1116009340 | 6/1999 |
| JP | 1116009341 | 6/1999 |
| JP | H11253401 | 9/1999 |
| JP | 2000171727 A | 6/2000 |
| JP | 2000330015 A | 11/2000 |
| JP | 2001061762 | 3/2001 |
| JP | 2001198086 | 7/2001 |
| JP | 2002000559 | 1/2002 |
| JP | 2002017667 | 1/2002 |
| JP | 2002058636 | 2/2002 |
| JP | 200265589 A | 3/2002 |
| JP | 2002065575 | 3/2002 |
| JP | 2002078675 | 3/2002 |
| JP | 2002216902 | 8/2002 |
| JP | 2002291693 | 10/2002 |
| JP | 2003038431 | 2/2003 |
| JP | 2003061900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049754 | 2/2004 |
| JP | 2004049756 | 2/2004 |
| JP | 2004129834 | 4/2004 |
| JP | 2004205779 A | 7/2004 |
| JP | 2005013557 A | 1/2005 |
| JP | 2005058547 | 3/2005 |
| JP | 2005253543 | 9/2005 |
| JP | 2005323874 A | 11/2005 |
| JP | 3765500 | 2/2006 |
| JP | 2006068109 | 3/2006 |
| JP | 2006068109 A | 3/2006 |
| JP | 2006218155 | 8/2006 |
| JP | 2006280954 | 10/2006 |
| JP | 2006288758 | 10/2006 |
| JP | 2007020866 A | 2/2007 |
| JP | 2007185276 | 7/2007 |
| JP | 2008068025 | 3/2008 |
| JP | 2008118568 | 5/2008 |
| JP | 2008161569 A | 7/2008 |
| JP | 2008229204 | 10/2008 |
| JP | 2008257108 A | 10/2008 |
| JP | 2009233186 | 10/2009 |
| JP | 4445647 | 4/2010 |
| JP | 2010178766 A | 8/2010 |
| JP | 2010279539 | 12/2010 |
| WO | 9219148 A1 | 11/1992 |
| WO | 0052643 A1 | 9/2000 |
| WO | 0245595 | 6/2002 |
| WO | 2004026125 | 4/2004 |
| WO | 2005082228 A1 | 9/2005 |
| WO | 2006073581 | 7/2006 |
| WO | 2006105932 A1 | 10/2006 |
| WO | 2007113801 A2 | 10/2007 |
| WO | 2007087421 | 11/2007 |
| WO | 2007136859 A2 | 11/2007 |
| WO | 2008012813 A1 | 1/2008 |
| WO | 2008073243 | 6/2008 |
| WO | 2008093288 | 8/2008 |
| WO | 2008139770 | 11/2008 |
| WO | 2008155776 | 12/2008 |
| WO | 2008156623 | 12/2008 |
| WO | 2009009414 | 1/2009 |
| WO | 2009025843 | 2/2009 |
| WO | 2009040744 | 4/2009 |
| WO | 2009095915 | 8/2009 |
| WO | 2010021342 | 2/2010 |
| WO | 2010028612 | 3/2010 |
| WO | 2010045406 | 4/2010 |
| WO | 2010064506 | 6/2010 |
| WO | 2010066788 | 6/2010 |
| WO | 2010146587 | 12/2010 |
| WO | 2010146587 A1 | 12/2010 |
| WO | 2011008922 | 1/2011 |
| WO | 2011041724 | 4/2011 |
| WO | 2011083451 | 7/2011 |
| WO | 2011126812 | 10/2011 |
| WO | 2012038958 | 3/2012 |
| WO | 2012056453 | 5/2012 |
| WO | 2012077116 | 6/2012 |
| WO | 2012077117 | 6/2012 |
| WO | 2012088201 A2 | 6/2012 |
| WO | 2012103266 | 8/2012 |
| WO | 2012120507 | 9/2012 |
| WO | 2012153324 | 11/2012 |
| WO | 2013014673 | 1/2013 |
| WO | 2013024476 | 2/2013 |
| WO | 2013043704 | 3/2013 |
| WO | 2013128136 | 9/2013 |
| WO | 2013131578 | 9/2013 |
| WO | 2013144944 | 10/2013 |
| WO | 2014061023 | 4/2014 |

OTHER PUBLICATIONS

Second mage of an Endo Smart Cap, made by Medivators, and obtained from http://www.byrnemedical.com/prod/150L.jpg and advertised at http://www.medivators.com/products/endoscopy-procedure-products/irrigation-tubing/endo-smartcap%C2%AE.
Brochure for US Endoscopy's AquaShield Water Bottle System, 2010.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
International Search Report for PCT/EP2009/066726, Aug. 16, 2010.
International Search Report for PCT/IL2011/000832, May 16, 2012.
International Search Report for PCT/IL2011/050049, May 15, 2012.
International Search Report for PCT/IL2011/050050, May 16, 2012.
International Search Report for PCT/IL2012/050037, Jun. 1, 2012.
International Search Report for PCT/IL2012/050274, Nov. 15, 2012.
International Search Report for PCT/IL2012/050299, Nov. 15, 2012.
International Search Report for PCT/IL2013/050840, Feb. 2, 2014.

(56) References Cited

OTHER PUBLICATIONS

International Search Report of PCT/IL10/00476 mailed Sep. 27, 2010, 2 pages.
International Search Report of PCT/IL2011/000745, dated May 8, 2012.
Office Action dated May 1, 2015 for U.S. Appl. No. 13/992,021.
First Office Action for CN 2012800171292, dated Feb. 28, 2015.
Office Action dated Mar. 12, 2015 for U.S. Appl. No. 13/822,908.
Office Action dated Feb. 13, 2015 for U.S. Appl. No. 13/713,449.
Office Action dated Feb. 17, 2015 for U.S. Appl. No. 13/882,004.
Office Action dated Mar. 6, 2015 for U.S. Appl. No. 13/413,059.
Office Action dated Nov. 26, 2014 for U.S. Appl. No. 13/713,466.
Office Action dated Jun. 3, 2015 for U.S. Appl. No. 13/992,014.
Office Action dated Jan. 15, 2015 for U.S. Appl. No. 13/190,968.
Notice of Allowance dated Jun. 8, 2015 for U.S. Appl. No. 13/984,028.
Notice of Allowance dated Jun. 8, 2015 for U.S. Appl. No. 13/413,252.
Prosecution File History for U.S. Appl. No. 13/190,968; Jul. 26, 2011 through Jun. 17, 2015.
Notice of Allowance dated Jun. 17, 2015 for U.S. Appl. No. 13/190,968.
Office Action dated Jul. 21, 2015 for U.S. Appl. No. 13/992,021.
Notice of Allowance dated Dec. 23, 2015 for U.S. Appl. No. 13/992,021.
Office Action for Japanese Patent Application No. JP2014-525562, dated Apr. 26, 2016.
Office Action for Japanese Patent Application No. JP2014-522214, dated Apr. 26, 2016.
Office Action dated Aug. 27, 2015 for U.S. Appl. No. 13/655,120.
Supplementary European Search Report for EP11847191.1, Jan. 16, 2015.
Examination Search Report for Canadian Patent Application No. CA2765559, Jan. 18, 2016.
Office Action for Chinese Patent Application No. 201280038808.8, May 20, 2015.
Second Office Action for Chinese Patent Applicatio No. CN201280038808.8, Feb. 25, 2016.
Office Action dated Aug. 6, 2015 for U.S. Appl. No. 13/119,032.
First Office Action for CN 2012800368972, Jun. 1, 2015.
Examination Report for Canadian Patent Application No. CA2765559, Jan. 18, 2016.
Corrected European Search Opinion for EP14186113.8, Apr. 29, 2015.
Extended European Search Report for EP12817452.1, Mar. 9, 2015.
Office Action dated Aug. 19, 2015 for U.S. Appl. No. 13/713,466.
Office Action dated Aug. 5, 2015 for U.S. Appl. No. 13/212,627.
Office Action for Chinese Patent Application No. 201180067259.2, May 29, 2015.
Office Action dated Aug. 18, 2015 for U.S. Appl. No. 13/713,449.
First office action for CN2011800627366, Feb. 25, 2015.
Supplementary European Search Report for European Application No. EP12823972, May 13, 2015.
Extended European Search Report for EP14186113.8, Apr. 1, 2015.
Notice of Allowance dated Dec. 15, 2014 for U.S. Appl. No. 13/713,466.
Notice of Allowance dated Dec. 15, 2015 for U.S. Appl. No. 13/713,466.
Office Action dated Jan. 12, 2016 for U.S. Appl. No. 13/713,466.
Office Action for Japanese Patent Application No. 2013-542668, Oct. 1, 2015.
Office Action for Japanese Patent Application No. 2013-535586, Sep. 24, 2015.
Second office action for Chinese Patent Application No. 201180062736.6, Oct. 12, 2015.
Office Action dated Dec. 4, 2015 for U.S. Appl. No. 13/822,908.
Office Action dated Nov. 24, 2015 for U.S. Appl. No. 13/413,059.
Office Action dated Nov. 3, 2015 for U.S. Appl. No. 13/992,014.
Office Action dated Oct. 7, 2015 for U.S. Appl. No. 13/882,004.
Extended European Search Report for EP11846069.0, Apr. 24, 2014.
First Office Action for Chinese Patent Applicatio No. CN201380053351.2, Mar. 2, 2016.

\* cited by examiner

CONNECTOR FOR USE WITH ENDOSCOPE

FIELD

The present application discloses a connector for use in medical devices. More particularly, the present application discloses disposable tubing joint cover connection apparatuses and methods of attachment between a tubing set and an endoscope.

BACKGROUND

An endoscope is a medical instrument used for examining and treating internal body parts such as the alimentary canals, airways, the gastrointestinal system, and other organ systems. Conventional endoscopes have at least a flexible tube carrying a fiber optic light guide for directing light from an external light source situated at a proximal end of the tube to a distal tip. Also, most endoscopes are provided with one or more channels, through which medical devices, such as forceps, probes, and other tools, may be passed. Further, during an endoscopic procedure, fluids, such as water, saline, drugs, contrast material, dyes, or emulsifiers are often introduced or evacuated via the flexible tube. A plurality of channels, one each for introduction and suctioning of liquids, may be provided within the flexible tube.

Usually, endoscopes also include a connector section for connecting the flexible tube to one or more of an electrical system, a light system, a water or other fluid system, and/or a suction system, which may be collectively termed as the control section of the endoscope. U.S. Pat. No. 4,753,222 discloses a flexible tube applied to an endoscope. U.S. Pat. No. 4,753,222 discloses a construction of a flexible tube, which is applied to an insertion section of an endoscope, adapted to be inserted into the body cavity. The flexible tube comprises a spiral tube formed by transforming a belt-shaped metal member into a spiral, a braid formed of fibers intertwined like a net, and fitted on the outer peripheral surface of the spiral tube, and a sheath covering the outer peripheral surface of the braid, and having a multilayer structure composed of inner and outer layers, at least for part of its length. The inner layer is a tube member which is formed of a high-polymer material, and is fitted on the outer peripheral surface of the braid. The outer layer is formed by applying a molten high-polymer material to the outer peripheral surface of the tube member, for cross-linking.

The flexible tube may be attached to the control section of an endoscope directly via a surface to surface tubing port interface. However, such direct connection may not provide an effective sealing between the air and water carrying channels when an acceptable maximum insertion force is applied during operation of the endoscope.

Alternately, conventional connector designs employ single 'o-ring' connectors in tube to endoscope connections for sealing off the water/fluid carrying channels. U.S. Pat. No. 7,841,880 discloses a connector for an endoscope which includes O-ring. U.S. Pat. No. 6,582,361 discloses a watertight cap which is detachably attached to a connector of an endoscope, the watertight cap comprising an external cylinder having an engaging part being detachably engaged with an outer periphery of a shell member provided around a connector pin of the connector and an internal cylinder arranged inside the external cylinder, an end of the internal cylinder being closed, the internal cylinder having a seal member being pressed against an inner periphery of the shell member, wherein a discharge hole opening to outside is formed between the external cylinder and the internal cylinder when the watertight cap is attached on the connector.

An O-ring seal maybe used in endoscope connectors as the seal allows a high local stress, and is capable of containing high pressure. However, it has been observed that it is difficult to maintain the seal integrity during multiple insertions of the endoscope tube into a body cavity. Since pressure in varying degrees is applied to the endoscope during operation, the use of a conventional o-ring design may result in failure of the seal or may require such a tight fit that causes difficulty in inserting the connector onto the air and water ports.

Hence, there is need for a connector that enables efficient and leak proof connection between an endoscope and one or more flexible tubing sets. There is also a need for a connector that can withstand normal endoscope working pressures without the seal integrity being compromised. Further, there is need for a connector that may be used to connect endoscope ports to one or more tubing sets with a minimal application of force.

SUMMARY

In one embodiment, the present application discloses a joint interface for connecting a first port of an endoscope and a second port of an endoscope to a connector, made of a material, having a first conduit and a second conduit, wherein said joint interface comprises a molded component and wherein said molded component comprises: a) a first connector channel adapted to receive said first port, wherein said first connector channel comprises a first end attached to a portion of said connector and wherein said first channel has a second end comprising a first o-ring and a second o-ring; and b) a second connector channel adapted to receive said second port, wherein said second connector channel comprises a first end attached to a portion of said connector and wherein said second channel has a third o-ring and a fourth o-ring.

Optionally, the joint interface comprises material that is more physically compliant than the material of said connector. The connector is rigid. The connector is a Y connector having the first conduit positioned at an angle relative to said second conduit. The second connector channel comprises a first channel portion and a second channel portion, wherein the second channel portion has a smaller diameter than the first channel portion and wherein the second channel portion comprises said third o-ring and said fourth o-ring. The molded component is formed by overmolding said molded component onto the connector. The diameter of the first o-ring is equal to a diameter of the second o-ring. The diameter of the third o-ring is equal to a diameter of the fourth o-ring. The first and the second o-rings are separated by a predefined distance.

Optionally, the first port of the endoscope is securely connected to the first connector channel via the first and the second o-rings and wherein said secure connection is leak proof and capable of withstanding a predetermined operational pressure. The second port of the endoscope is securely connected with the second connector channel via the third and the fourth o-rings and wherein said secure connection is leak proof and capable of withstanding a predetermined operational pressure. The first and the second o-rings are configured to be compressed during connection with the first port of the endoscope. The third and the fourth o-rings are configured to be compressed during connection with the second port of the endoscope.

In another embodiment, the present application discloses a connector for connecting a first port of an endoscope and a second port of an endoscope to a tubing set, comprising: a component, made of a material, comprising a first conduit and a second conduit; and a compliant interface, wherein said compliant interface comprises a) a first connector channel adapted to receive said first port, wherein said first connector channel is in fluid communication with the first conduit and wherein said first channel has at least two o-rings; and b) a second connector channel adapted to receive said second port, wherein said second connector channel is in fluid communication with the second conduit and wherein said second channel has at least two o-rings.

Optionally, the compliant interface comprises material that is less rigid than the material of said component. The component is a Y connector having the first conduit positioned at an angle relative to said second conduit. The second connector channel comprises a first channel portion and a second channel portion, wherein the second channel portion has a smaller diameter than the first channel portion and wherein the second channel portion comprises a third o-ring and a fourth o-ring. The compliant interface is formed by overmolding said compliant interface onto the component. The first connector channel comprises a first o-ring and a second o-ring and wherein a diameter of the first o-ring is equal to a diameter of the second o-ring. The diameter of the third o-ring is equal to a diameter of the fourth o-ring. The first and the second o-rings are separated by a predefined distance.

Optionally, the first port of the endoscope is securely connected to the first connector channel via the first and the second o-rings and wherein said secure connection is leak proof and capable of withstanding a predetermined operational pressure. The second port of the endoscope is securely connected with the second connector channel via the third and the fourth o-rings and wherein said secure connection is leak proof and capable of withstanding a predetermined operational pressure. The first and the second o-rings are configured to be compressed during connection with the first port of the endoscope. The third and the fourth o-rings are configured to be compressed during connection with the second port of the endoscope.

The aforementioned and other embodiments of the present shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

Figure 1A:
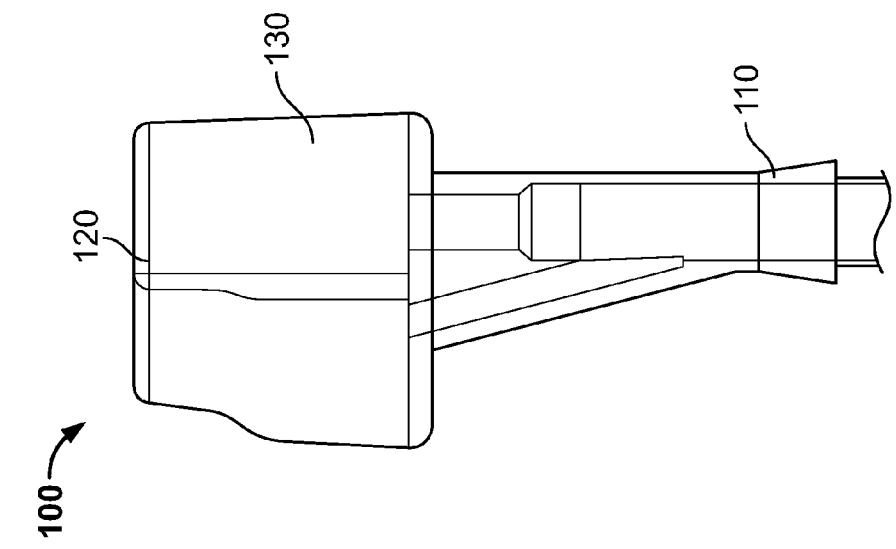
FIG. 1A illustrates an internal view of a joint cover connector, in accordance with one embodiment.

The present specification discloses a disposable tubing joint cover enabling connection between a tubing set and an endoscope. The joint cover embodiments disclosed herein comprise dual o-ring seals that enable efficient and leak proof connection between an endoscope comprising, among other features, an irrigation port and corresponding flexible tubing.

The present specification discloses multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

A control section of an endoscope comprises one or more ports for connecting with one or more tubing sets which are used to carry water or provide suction during an endoscopic procedure. Traditional seal integrity designs typically rely on a surface-to-surface tubing to port interface, which are very difficult to maintain a seal while still achieving acceptable insertion force values, or single o-ring connector designs, which are difficult to maintain seal integrity during multiple insertions and which are compromised during movement of tubing set to endoscope.

As is commonly known in the art, an o-ring is also known as a packing, or a toric joint, and is a mechanical gasket in the shape of a torus. More specifically, it is a loop of a material, typically an elastomer, with a disc-shaped cross-section, designed to be seated in a groove and compressed during assembly between two or more parts, thereby creating a seal at the interface of the two or more parts. An o-ring may be used in static applications or in dynamic applications where there is relative motion between the parts and the o-ring. O-rings can seal large magnitudes of pressure.

The present specification discloses a connector system that includes two connector channels and is shaped in the form of a joint cover that may be fitted around the endoscope ports for receiving one or more tubes. The joint cover connector comprises dual o-ring seals designed to fit snugly around the endoscope ports and provide an air tight seal while withstanding a threshold level of pressure generated during operation of the endoscope. The use of two o-ring seals placed in an aligned position with a predetermined gap separating the seals enables tubing to be connected to the endoscope with reduced force, as compared with prior art connection techniques, while still maintaining a sufficient seal pressure. The incorporation of dual o-rings into each connector channel facilitates the seal between the endoscope irrigation and suction ports, on the one hand, and the tubing set access channels, on the other hand. In various embodiments, the interface between the dual o-rings and both channels prevent seal integrity failures when a side load is placed on the joint cover connector and also allows for ease of connection to the endoscope. A single o-ring design does not protect against this type of failure.

By employing a dual o-ring design, the connector has a reduced amount of force required to connect the tubing set connector to the endoscope while maintaining a homogeneous seal that will withstand normal endoscope functioning pressures. Dual o-ring design acts as a fulcrum/seal, allowing displacement and pliability to the access ports during movement of the tubing set in reference to the endoscope irrigation and suction ports while minimizing the overall side to side displacement. Benefits include a) increased pliability to the seal between the tubing set and endoscope relative to a single o-ring design, b) a more forgiving internal diameter which reduces the force required to connect the tubing set to the endoscope, c) an increase in the surface area contact of the o-rings to endoscope ports, thus increasing the seal integrity, d) seal integrity during offset displacement of endoscope ports which occurs during movement of tubing set to endoscope, and e) minimized fatigue of o-ring integrity during multiple connections of tubing sets to endoscopes during a 24 hour window of product use.

Additionally, as further described below, the connector comprises a flexible portion, which includes the dual o-ring connector portion, with a more rigid portion to which air and fluid tubing are connected. The combined flexible and rigid structure provides for a flexible interface that is easy to connect to endoscope ports, while still maintaining overall structural integrity through the rigid portion.

FIG. 1A illustrates an internal view of a joint cover connector, in accordance with one embodiment of the present invention. As illustrated, the joint cover connector 100 comprises a compliant interface 109 which has been overmolded onto a rigid Y connector 101. The rigid Y connector 101 comprises a first section 104 and a second section 102. The first section 104 is physically adhered to, by virtue of an overmolding process, to a first channel 114 having an o-ring 108 structure leading to an aperture 104b on the distal end. The second section 102 is physically adhered to, by virtue of an overmolding process, to a second channel 115 having an o-ring 106 leading to an aperture 102b on the distal end.

The distal end 104b of the first channel 114 fits around a first port of an endoscope and the distal end 102b of the second channel 115 fits around a second port of the endoscope. In various embodiments, the joint cover connector is compatible with all available endoscope designs that have air and water ports.

The proximal end 104a of the first channel 114 is fixedly attached to the distal end 105 of a first portion 107 of a Y connector 101 and the proximal end 102a of the second channel 115 is fixedly attached to the distal end 103 of a second portion 108 of the Y connector 101. The first portion 107 of the Y connector joint 101, which defines a first conduit, extends downward and connects to the second portion 108 of the Y connector joint 101, which defines a second conduit, at an angled juncture 111. In one embodiment, the Y connector joint 101 may be used to introduce into an endoscope, through the first conduit 107 and channel 114 and/or second conduit 108 and channel 115, water, or any other fluid, via the joint cover connector system 100. In various embodiments, the "Y" connector joint is rigid, is made out of polycarbonate and is injection molded using conventional injection molding processes.

Both channels 114 and 115 comprise dual o-ring seals 108 and 106 respectively. The dual o-ring seals 106, 108 provide a strong sealing action between the endoscope's irrigation and suction ports and tubing set 101 and its access conduits 107, 108, which access the joint cover connector system 100 through the proximal ends 104a, 102a, of the first and second channels, 114, 115. The distal end 102b of the second channel 115 fits around, and snugly attaches to, a first port of an endoscope and the distal end 104b of the first channel 114 fits around, and snugly attaches to, a second port of the endoscope.

Figure 1B:
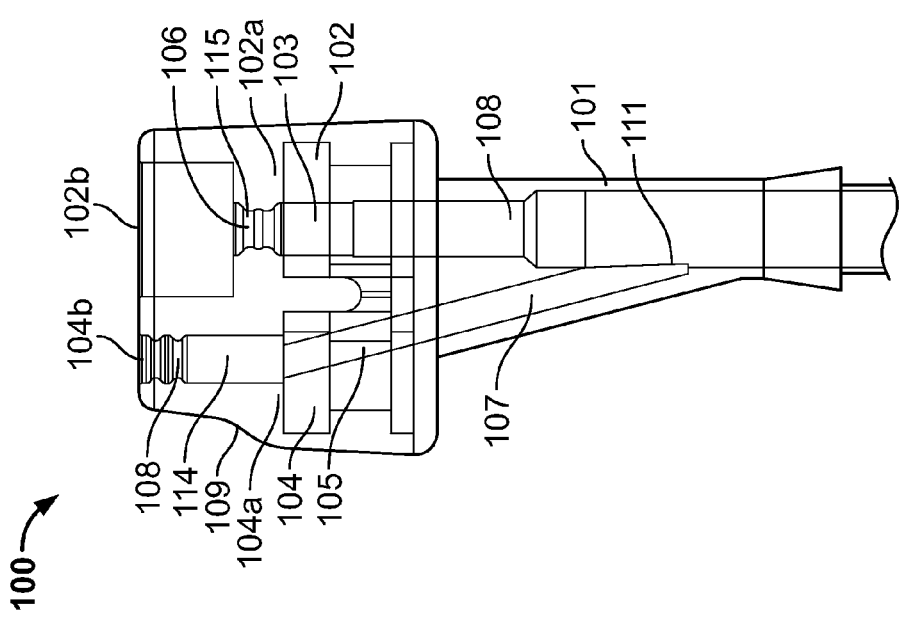
FIG. 1B illustrates a front opaque view of the joint cover connector, in accordance with one embodiment.

FIG. 1B illustrates a front opaque view of the joint cover connector system 100, in accordance with one embodiment. A connecting portion of a standard endoscope is fitted into the joint cover connector 100 through end 120 while a tubing set is fixedly attached to the joint cover connector 100 through the end of Y-connector 110. Referring to FIGS. 1A and 1B, the dual o-ring seals 106 and 108 cause the joint cover connector system 100 to securely attach to the corresponding ports of an endoscope. In both cases, except for the spacing created by, and defined within, channels 114, 115 and conduits 107, 108 through which fluid or air flows are applied, the joint cover connector system is a solid structure with all of the volume between the periphery or surface 130 of the joint cover connector system and the internal channels or conduits being filled by plastic, or more specifically, an elastomer or moldable material. In another embodiment, there may be areas within the joint cover connector system, other than the internal channels or conduits that have voids, spaces, or are otherwise not filled with material.

By employing the dual o-ring seals 106, 108 a measure of force required to connect the tubing set 101 to an endoscope while maintaining a homogeneous seal that would withstand normal endoscope functioning pressures, is reduced by a predefined amount. As stated above, the flexible portion of the joint cover connector 100 combines with a more rigid Y-connector 110 to yield a structure that provides for a flexible interface which is easy to connect to endoscope ports, while still maintaining overall structural integrity through the rigid portion.

In various embodiments, with the use of two o-rings the internal diameters of the channels that mate with the air or water ports may be made larger than when using a single o-ring. Hence, the channel and tubing interfaces are looser with the use of two o-rings. In order to obtain the same seal integrity with a single o-ring the internal diameters of the channels that mate with the air or water ports would have to be smaller (tighter interface) which would require greater force to make the connection between the joint connector and the endoscope air and water ports.

Figure 2A:
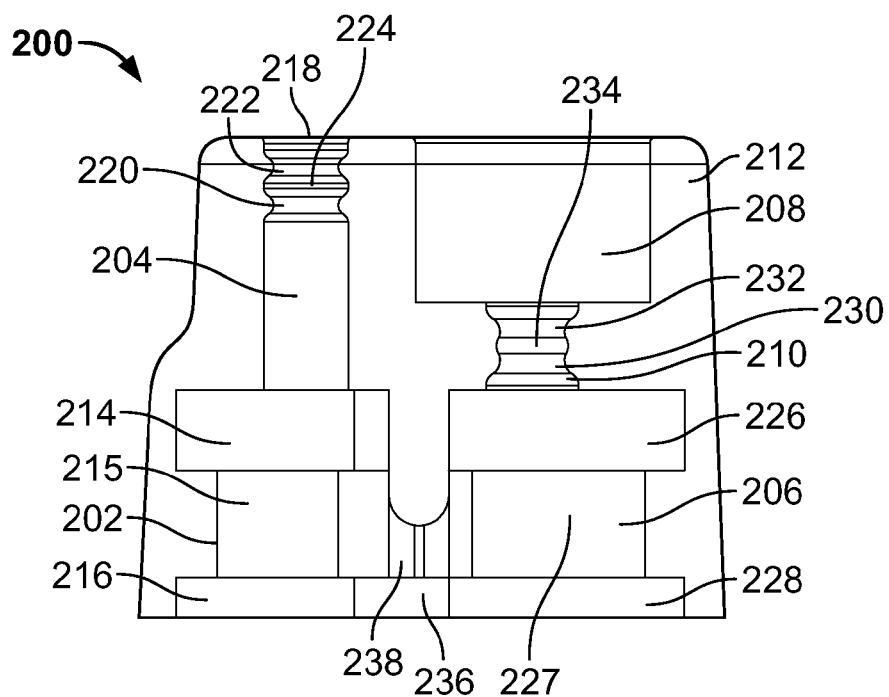
FIG. 2A illustrates yet another view of the joint cover connector, in accordance with one embodiment.

FIG. 2A illustrates yet another view of the joint cover connector system 200 without the Y joint structure comprising the first and second conduits, in accordance with one embodiment. The joint cover connector system 200 comprises a first channel and a second channel that are overmolded onto a rigid base that functions as the distal portion of the rigid Y connector. The rigid base comprises a first base 202. The first base 202 is coupled with a first channel 204. The rigid base further comprises a second base 206. The second base 206 is coupled with a second channel 208 via a third channel 210. The first, second, and third channels 204, 208, 210 are defined by voids or spaces in a molded plastic casing 212 which is solid from the sections to the surface of the casing 212.

As illustrated, the first base 202 comprises an upper end 214 and a lower end 216 which have an equal diameter which is more than a diameter of a middle portion 215 of the base 202. A lower end of the first channel 204 is connected to the upper end 214 of the first base 202. The lower end 216 is fixedly attached to a remaining portion of the rigid Y-connector that extends out from the molded, flexible casing 212.

An upper end 218 of the first channel 204 comprises a pair of o-rings 220, 222. The o-rings 220 and 222 have an equal diameter and thickness. The upper end 218 of the first channel 204 is configured to interface with an endoscope port through which water, or any other fluid, may be introduced. As illustrated, the o-rings 220, 222 are part of the molded channel structures in the joint cover connector near the upper end 218 of the first channel 204. The two o-rings 220, 222 are separated by a predetermined distance and a portion 224 of the first channel 204 lying between the two o-rings 220 and 222.

In an embodiment, the first channel 214 receives an air port of an endoscope while the second channel 208 receives a water port. The second base 206 comprises an upper end 226 and a lower end 228 which have an equal diameter and which are more than a diameter of a middle portion 227 of the base 206. In an embodiment, the upper, middle and lower portions of the second base 206 is thicker than corresponding upper, middle and lower portions of the first base 202. The lower end 228 is fixedly attached to a remaining portion of the rigid Y-connector that extends out from the molded, flexible casing 212.

A lower end of the third channel 210 is connected to the upper end 226 of the second base 206. An upper end of the third channel 210 is connected with a lower end of the second channel 208. An upper end of the second channel 208 receives a port of an endoscope. The third channel 210 comprises a pair of o-rings 230, 232. The o-rings 230 and 232 have an equal diameter and thickness. As illustrated, the o-rings 230, 232 are part of the molded middle portion of the third channel 210. The two o-rings 230, 232 are separated by a predetermined distance and a portion 234 of the third channel 210 lying between the two o-rings 230 and 232.

In the illustrated embodiment, the lower portion 216 of the first base 202 and the lower portion 228 of the second base 206 are connected by a rigid connecting strip 236. Further the first and the second bases 202 and 206 are also connected at a middle location via a rigid curved connecting member 238. The curved connecting member 238 comprises a lower flat end which is connected with an upper end of the connecting strip 236; and an upper curved end. The sides of the curved connecting member 238 are connected with a side each of the first and the second bases 202, 206 as illustrated. In various embodiments, the curved connecting member 238 is a support truss and may be of a plurality of shapes and designs. In an embodiment, the connecting strip 236 and the curved connecting member 238 are physically and permanently attached to the first and the second bases 202, 206 and are made of the same rigid material as the first and the second bases 202, 206.

Figure 2B:
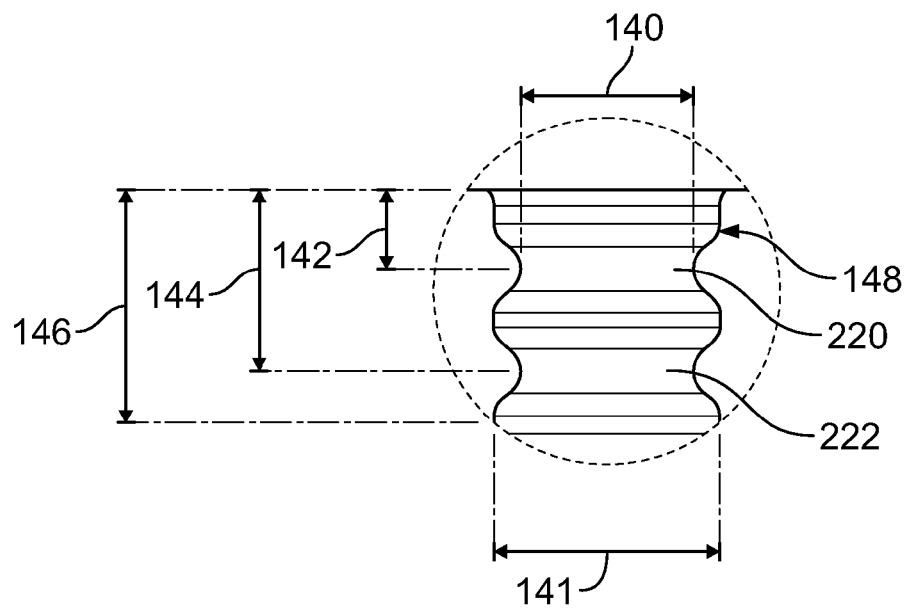
FIG. 2B illustrates the dual o-rings 220, 222 used in the joint cover connecter system 200, in accordance with one embodiment.
Figure 2C:
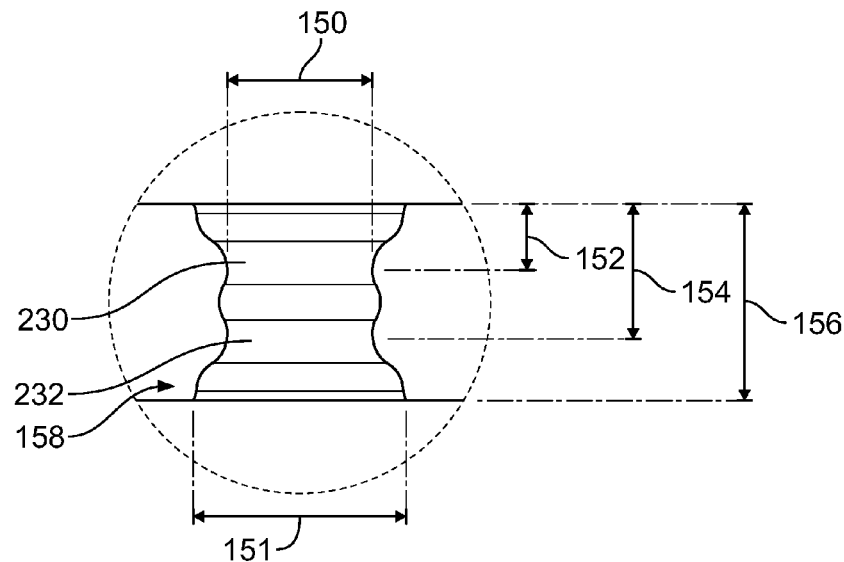
FIG. 2C illustrates the dual o-rings 230, 232 used in the joint cover connecter system 200, in accordance with one embodiment.

FIG. 2B illustrates the dual o-rings 220, 222 used in the joint cover connecter system 200, in accordance with an embodiment of the present invention. As illustrated an internal diameter 140 of the o-rings is approximately 2.4 mm while the external diameter 141 is 3.15 mm. The radius 148 of the o-rings is 0.375 mm. The lengths of sections 142, 144 and 146 are 1.1, 10.08 and 3.17 mm respectively. FIG. 2C illustrates the dual o-rings 230, 232 used in the joint cover connecter system, in accordance with an embodiment of the present invention. As illustrated an internal diameter 150 of the o-rings is approximately 2.4 mm while the external diameter 151 is 3.45 mm. The lengths of sections 152, 154 and 156 are 1.1, 2.2 and 3.3 mm respectively. The radius 158 of the o-rings is 0.525 mm. In an embodiment, the internal diameters of the dual o-rings used for both the water and the air ports are the same. Also, in various embodiments the material used for constructing the joint cover connector is poly vinyl chloride (PVC) 70A.

Figure 2D:
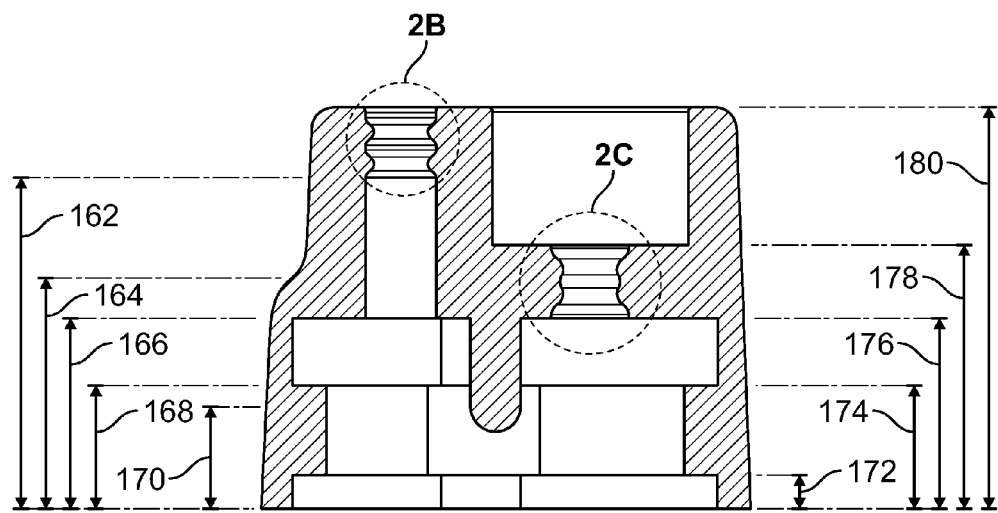
FIG. 2D illustrates yet another view of the joint cover connector system 200, in accordance with one embodiment.

FIG. 2D illustrates yet another view of the joint cover connector system, in accordance with one embodiment of the present invention. As illustrated the lengths of sections 162, 164, 166, 168, 170 are 14.83, 10, 8.5, 5.5, 4.49 respectively and sections 172, 174, 176, 178, and 180 are 1.5, 5.5, 8.5, 11.8 and 18 mm respectively.

Figure 3:
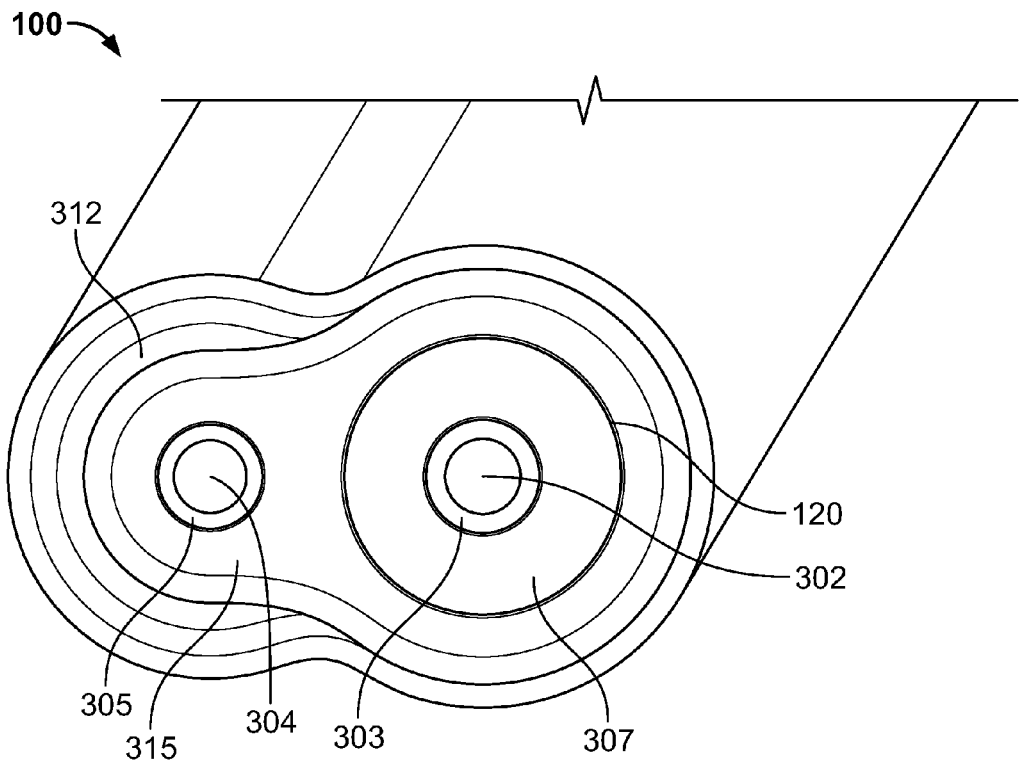
FIG. 3 illustrates a top view of the joint cover connector, in accordance with one embodiment.

FIG. 3 illustrates a view of the joint cover connector system 100, in accordance with one embodiment. FIG. 3 illustrates a view of one end 120 of the joint cover connector system 100. An aperture 302 receives a first port of an endoscope, whereas an aperture 304 receives a second port of an endoscope.

In an embodiment, the aperture 302 is an upper end of a first channel comprising a first pair of o-rings for providing an air-tight seal to the first endoscope port. Also, in an embodiment, the aperture 304 is an upper end of a second channel which has a lower end that in turn is connected with a third channel comprising a second pair of o-rings for providing an air-tight seal to the second endoscope port. Aperture 304 preferably is defined by a ring of elastomeric material 305 that, relative to the connector joint cover surface 120 is indented or otherwise depressed. Similarly, aperture 302 preferably is defined by a ring of elastomeric material 303 that, relative to the connector joint cover surface 120 is indented or otherwise depressed.

The top end of the connector joint cover 120 is shaped in the form of two intersecting circles, or a figure eight placed on its side. One side, which defines aperture 302, has a ring of material, 307 distinct from the material that comprises the end of the joint cover 120 and the depressed internal ring 303. The second side, which defines aperture 304, has a depressed portion 312 that curves up and a surface 315 that surrounds aperture 304.

Figure 4:
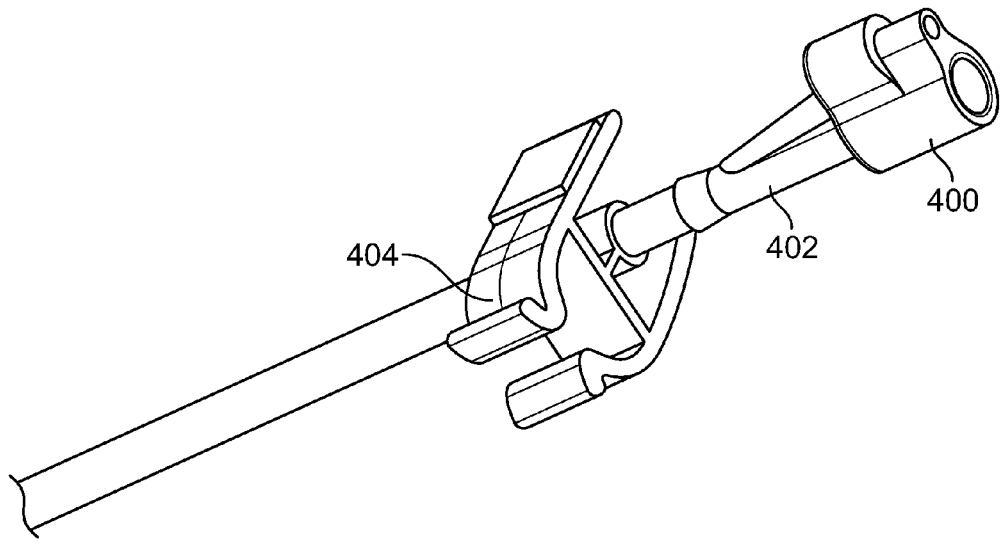
FIG. 4 illustrates the joint cover connector coupled with a tubing set to be used with an endoscope, in accordance with one embodiment.

FIG. 4 illustrates the joint cover connector 400 coupled with a tubing set 402 to be used with an endoscope, in accordance with one embodiment. As illustrated, a joint cover connector system 400 is coupled with tubing set 402 which in turn is attached to other structures using a clip 404. In an embodiment, the tubing set 402 may be connected to a joint cover of a bottle containing sterile water that is delivered to a control section of an endoscope via the joint cover connector 400.

It should be appreciated that the joint cover connector comprises a compliant interface and rigid Y joint section where the compliant interface is a single molded part in which the O-rings are molded as part of the compliant interface. Operationally, the rigid Y joint section is made using a conventional molding process. The compliant interface is then overmolded on the rigid Y joint section with core pins used to mold the o-ring channel shape. The O-rings are molded as part of the molding of the compliant interface, not inserted or created after the compliant interface is created.

Furthermore, it should be appreciated that the joint cover connector of the present invention provides a sturdier seal between a tubing set and an endoscope as compared to prior art connectors having a single o-ring design. The seal is more resilient and can withstand normal endoscope working pressures. The joint cover connector comprises an internal diameter which reduces the force required to connect a tubing set to an endoscope.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A connector device for connecting a first port of an endoscope and a second port of an endoscope to a plurality of tubing, wherein the connector device comprises:
  a rigid portion, wherein said rigid portion comprises a tubing connector having a first conduit and a second conduit, wherein, at a first end of the tubing connector, the first conduit and second conduit are in a parallel relationship and wherein, at a second end, the first conduit and second conduit are in a non-parallel relationship and terminate in a base; and
  a flexible portion, wherein the flexible portion is a molded component and comprises:
    a first connector channel adapted to receive said first port, wherein said first connector channel comprises a first end attached to a first portion of said base, wherein said first channel has a second end comprising a first seal formed integrally of a first o-ring and a second o-ring, wherein the first and the second o-rings are made of elastomeric material and configured to be compressed during connection with the first port of the endoscope and wherein a material of the first seal extends between the first and second o-rings to separate the first and second o-rings by a predefined distance; and
    a second connector channel adapted to receive said second port, wherein said second connector channel comprises a first end attached to a second portion of said base, wherein said second channel has a second seal formed integrally of a third o-ring and a fourth o-ring, wherein the third and the fourth o-rings are made of elastomeric material and are configured to be compressed during connection with the second port of the endoscope, and wherein a material of the second seal extends between the third and fourth o-rings to separate the third and fourth o-rings by a predefined distance.

2. The connector device of claim 1 wherein said tubing connector is a Y connector having the first conduit positioned at an acute angle relative to said second conduit.

3. The connector device of claim 1 wherein the second connector channel comprises a first channel portion and a second channel portion, wherein the second channel portion has a smaller diameter than the first channel portion and wherein the second channel portion comprises said third o-ring and said fourth o-ring.

4. The connector device of claim 1, wherein the flexible portion is formed by overmolding said molded component onto the base.

5. The connector device of claim 1, wherein a diameter of the first o-ring is equal to a diameter of the second o-ring.

6. The connector device of claim 1, wherein a diameter of the third o-ring is equal to a diameter of the fourth o-ring.

7. The connector device of claim 1, wherein the first port of the endoscope is securely connected to the first connector channel via the first and the second o-rings and wherein said secure connection is leak proof and capable of withstanding a predetermined operational pressure.

8. The connector device of claim 1, wherein the second port of the endoscope is securely connected with the second connector channel via the third and the fourth o-rings and wherein said secure connection is leak proof and capable of withstanding a predetermined operational pressure.

9. A connector for connecting a first port of an endoscope and a second port of an endoscope to a tubing set, comprising:
  a rigid component, made of a first material, comprising a Y connector and having a first conduit and a second conduit extending therethrough, wherein, at a first end of the Y connector, the first conduit and the second conduit are in a parallel relationship and wherein, at a second end, the first conduit and second conduit are in a non-parallel relationship and terminate in a base; and
  a compliant interface positioned on said base and comprising a second material that is more flexible than said first material, wherein said compliant interface comprises:
    a first connector channel adapted to receive said first port, wherein said first connector channel is in fluid communication with the first conduit, wherein said first channel has a first seal formed integrally of a first and second o-rings wherein the first and the second o-rings are made of elastomeric material and configured to be compressed during connection with the first port of the endoscope and wherein a material of the first seal extends between the first and the second o-rings to separate the first and second o-rings by a predefined distance; and
    a second connector channel adapted to receive said second port, wherein said second connector channel is in fluid communication with the second conduit, wherein said second channel has a second seal formed integrally of a third and fourth o-rings, wherein the third and the fourth o-rings are made of elastomeric material and configured to be compressed during connection with the second port of the endoscope and wherein a material of the second seal extends between the third and the fourth o-rings to separate the third and fourth o-rings by a predefined distance.

10. The connector of claim 9 wherein the second connector channel comprises a first channel portion and a second channel portion, wherein the second channel portion has a smaller diameter than the first channel portion and wherein the second channel portion comprises the third o-ring and the fourth o-ring.

11. The connector of claim 9, wherein the compliant interface is formed by over-molding said second material onto the rigid component.

12. The connector of claim 9, wherein a diameter of the first o-ring is equal to a diameter of the second o-ring.

13. The connector of claim 10, wherein a diameter of the third o-ring is equal to a diameter of the fourth o-ring.

14. The connector of claim 9, wherein the first port of the endoscope is securely connected to the first connector channel via the first and the second o-rings and wherein said secure connection is leak proof and capable of withstanding a predetermined operational pressure.

15. The connector of claim 13, wherein the second port of the endoscope is securely connected with the second connector channel via the third and the fourth o-rings and wherein said secure connection is leak proof and capable of withstanding a predetermined operational pressure.

* * * * *